United States Patent [19]

Kato et al.

[11] Patent Number: 4,543,211
[45] Date of Patent: Sep. 24, 1985

[54] CONJUGATE HAVING CYTOTOXICITY AND PROCESS FOR THE PREPARATION THEREOF

[75] Inventors: Yoshinori Kato; Naoji Umemoto, both of Hino; Takeshi Hara, Hachioji; Yutaka Tsukada, Ebetsu; Hidematsu Hirai, Sapporo, all of Japan

[73] Assignee: Teijin Limited, Osaka, Japan

[21] Appl. No.: 563,858

[22] Filed: Dec. 21, 1983

[30] Foreign Application Priority Data

Dec. 24, 1982 [JP] Japan ................. 57-226237

[51] Int. Cl.⁴ ................ C07G 7/00; C07C 103/52; A61K 39/44; A61K 39/395
[52] U.S. Cl. ................ 260/112 B; 260/112 R; 424/85; 525/54.1; 514/12
[58] Field of Search ............ 260/112 B, 112 R; 424/85, 177; 525/54.1

[56] References Cited

U.S. PATENT DOCUMENTS

| | | | |
|---|---|---|---|
| 4,017,471 | 4/1977 | Davies | 260/112 B |
| 4,046,722 | 9/1977 | Rowland | 260/112 B |
| 4,093,607 | 6/1978 | Sela et al. | 260/112 P |
| 4,263,279 | 4/1981 | Sela et al. | 424/85 |
| 4,315,851 | 2/1982 | Yoshikumi et al. | 260/112 B |
| 4,340,535 | 7/1982 | Voisin et al. | 260/112 B |
| 4,350,626 | 9/1982 | Masuho et al. | 424/177 X |
| 4,363,758 | 12/1982 | Masuho et al. | 260/112 B |
| 4,368,149 | 1/1983 | Masuho et al. | 260/112 B |
| 4,379,145 | 4/1983 | Masuho et al. | 424/177 |
| 4,401,592 | 8/1983 | Yoshikumi et al. | 260/112 B |

OTHER PUBLICATIONS

Nature, vol. 271, Feb. 1978, pp. 752–754, Thorpe et al.

Primary Examiner—Howard E. Schain
Attorney, Agent, or Firm—Sughrue, Mion, Zinn, Macpeak, and Seas

[57] ABSTRACT

A conjugate having cytotoxicity prepared by covalently binding a polymer which has cytotoxic substances linked to its side chains and a reactive group at its terminal to an immunoglobulin, or its fragment, which is capable of selectively binding to a particular antigen possessed by cells to be killed.

11 Claims, No Drawings

CONJUGATE HAVING CYTOTOXICITY AND PROCESS FOR THE PREPARATION THEREOF

BACKGROUND OF THE INVENTION

1. Field of the Invention

This invention relates to a novel conjugate having cytotoxicity and a process for the preparation thereof. More particularly, this invention relates to a novel conjugate having cytotoxicity comprising a constituent part consisting of an immunoglobulin capable of binding selectively to a particular antigen possessed by a cell to be killed (hereinafter referred to as target cell) or consisting of its fragment having a part which binds to such antigen and a constituent part consisting of a polymer carrying a cytotoxic substance linked thereto and a process for the preparation thereof. The conjugate having cytotoxicity obtained according to this invention is useful, for instance, as an antitumor agent which exerts an action on cancer cells selectively.

2. Description of the Prior Art

Many attempts have hitherto been made to bind cytotoxic substances of various kinds to an immunoglobulin, which is capable of binding selectively to a particular target cell, with the purpose of destroying certain kinds of cells selectively. For instance, a conjugate comprising an immunoglobulin having p-bis(2-chloroethyl)amino-L-phenylalanine, etc. linked thereto (Japanese Patent Application Laid-open No. 61640/76) a conjugate comprising an immunoglobulin having methotrexate linked thereto (Japanese Patent Application Laid-open No. 65829/81, a conjugate comprising an immunoglobulin having chlorambucil, etc. linked thereto (Japanese Patent Application Laid-open No. 65828/81), a conjugate comprising an immunoglobulin having mitomycin C, etc. linked thereto (Japanese Patent Application Laid-open No. 92325/80), and a conjugate comprising an immunoglobulin having daunomycin linked thereto (Japanese Patent Application Laid-open No. 144723/76) are publicly known.

These conjugates having cytotoxicity obtained according to the abovementioned methods are expected to bind selectively to a tumor cell and exert a toxic action on the tumor cell and accordingly may work as very useful drugs. However, in case where the cytotoxic substance is made to directly bind to the immunoglobulin, if the immunoglobulin has too much cytotoxic substance linked thereto, the activity of the immunoglobulin to recognize the antigen tends to become low, therefore, only a small amount of cytotoxic substance has to be bound to the immunoglobulin to avoid such problem.

There is, on the other hand, a probable assumption that the abovementioned problem can be improved upon when a polymer is used as an intermediate carrier of the cytotoxic substance. But a method described in Japanese Patent Application Laid-open No. 126281/76 presents another problem that, since the method includes the reaction in which a lot of cytotoxic substance is linked to the polymer carrier and another reaction in which the polymer-cytotoxic substance conjugate is linked to the immunoglobulin are both carried out at the same kinds of functional groups of the polymer, thus allowing the polymer carrier to bind to many immunoglobulins, the obtained conjugates not only fail to have a uniform structure and quality but also contain high molecular weight substances not useful as a therapeutic agent.

SUMMARY OF THE INVENTION

As the result of laborious study to correct such defects of the prior art, the inventors of this invention have come to find out that a conjugate having cytotoxicity, which is free from high molecular weight substances not useful as a therapeutic agent and comprises an immunoglobulin having a lot of cytotoxic substance linked thereto, can be obtained through the medium of a polymer carrier having only one reacting group which is to be used for the reaction of binding to an immunoglobulin and many other reacting groups which are to be used for binding of cytotoxic substance, whereby, after a lot of cytotoxic substance is linked to the polymer carrier through many reacting groups, the polymer carrier is made to bind to the immunoglobulin through said only one reactive group which is solely aimed for binding to the immunoglobulin, thus achieving the present invention.

The present invention is directed to a conjugate having cytotoxicity comprising an immunoglobulin, or its fragment, which is capable of selectively binding to a particular antigen possessed by a cell to be killed, and a polymer, which has cytotoxic substances linked to its side chains and a reactive group at its terminal, both being covalently bound to each other, and a process for the preparation thereof.

DESCRIPTION OF THE PREFERRED EMBODIMENTS

In the present invention, an immunoglobulin (guiding part of a conjugate having cytotoxicity) which is capable of selectively, or discriminately, binding to a particular antigen possessed by a cell to be killed includes the following. It is an immunoglobulin prepared from antisera isolated from a man or animals such as a monkey, horse, cow, goat, sheep, rabbit, guinea pig, hamster, rat, mouse, etc., which are immunized with such target cells as tumor cells or certain lymphocytes or tissues which contain any of them, by such a publicly known method as ethanol fractionation, ammonium sulfate fractionation, ion exchange chromatography, and gel filtration column chromatography; or a monoclonal antibody obtained from an immortalized cell prepared by cancerating antibody-producing cells collected from a man or an animal, which is immunized with the target cells, with the use of a virus or from a hybridoma prepared by fusing them with myeloma cells. An immunoglobulin, which is obtained by cleaving its binding to the target cell by use of a surface active agent, etc. and is specific to said target cell, is also included in the immunoglobulins of the present invention.

It is generally known that the immunoglobulin falls into five classes, i.e. IgG, IGA, IgM, IgD, and IgE, and that some of them consist of several subclasses. But they are common in their basic structure in that they consist of two heavy chains and two light chains and that they are composed of Fab moieties which have an activity of binding to an antigen and an Fc moiety which has an effector activity. However, IgM exists as a pentamer and IgA partially as a dimer.

As a guiding part of the conjugate having cytotoxicity, the whole of the immunoglobulin may be used and its fragrant may also be used so far as the fragment contains its antigen-binding part. As such antibody fragment, monomeric IgMs of IgM antibody and a fragment having no Fc part of the antibody, for instance, are used. IgMs is obtained, for instance, by reducing IgM by use of cysteine. IgMs has a special feature in that thiol functional group(s), which arise from a disulfide group binding IgMs to each other in the original IgM, can be used in linking IgMs to an albumin, and also in that IgMs is rather desirable to be used for preparing a stable agent having less tendency to aggregate as compared with IgM. In the conjugate, which contains an Fc part in it, the Fc part induces the indiscriminate adsorptive binding to cells other than target cells and also the binding to an Fc receptor on the cell membrane, thus reducing the capability of the conjugate having cytotoxicity to select cells to be killed. Furthermore, since the antigenecity of the immunoglobulin as a xenogeneic protein is especially strong at its Fc part, a fragment of the immunoglobulin having no Fc part is preferable to be used as a guiding part of the conjugate having cytotoxicity from a viewpoint of lowering the antigenecity of the conjugate. The cleavage of an immunoglobulin with a proteolytic enzyme such as papain, trypsin, chymotrypsin, plasmin, etc. generally gives what is called Fab fragment having one variable region. Also the peptic cleavage, or the tryptic cleavage depending upon the conditions, of an immunoglobulin gives what is called F(ab')$_2$ fragment having two variable regions. This fragment further turns to be monovalent Fab' fragments when it is treated with mercaptan. When the immunoglobulin is cleaved while being denatured, it gives the variable region only. The immunoglobulins and the aforementioned fragments arising from immunoglobulins can all be used as a guiding part of the conjugate of the present invention regardless of the class and subclass to which the material globulins belong.

Of the conjugates having cytotoxicity of the present invention prepared by covalently linking a polymer which is made to have a cytotoxic substance linked thereto, to an immunoglobulin or its fragment a conjugate expressed by the following formula (I) is a desirable one from the viewpoint of their preparation, purification and activity,

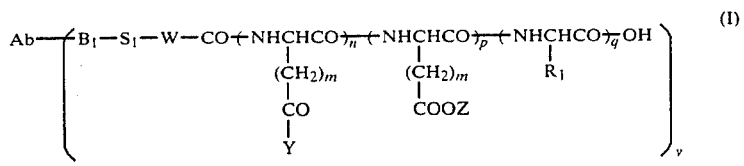

wherein Ab indicates an immunoglobulin or its fragment capable of binding selectively to a certain antigen possessed by a cell to be killed; $B_1$ is a divalent organic group; $S_1$ is a sulfur atom; W is a divalent organic group; $R_1$ indicates a side chain at the α-position of α-amino acid or its derivative (excluding a group which has a carboxyl group); Y represents a residue of a cytotoxic substance which contains an amino group or an imino group in the molecule resulting from the reaction of such groups; Z indicates a hydrogen atom or a monovalent cation; m is an integer 1 to 4; n, p, and q indicate the number of structural units, being n=5 to 1500, p=0 to 1500, and q=0 to 1500 respectively; and v indicates an integer 1 to 10:

furthermore, a conjugate expressed by the following formula (II)

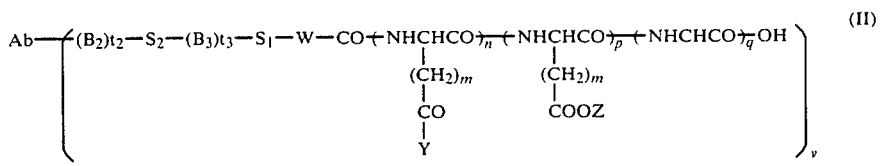

wherein definitions of Ab, $S_1$, W, $R_1$, Y, Z, m, n, p, q, and v are the same as those given in case of formula (I); $S_2$ indicates a sulfur atom; $B_2$ and $B_3$ are divalent organic groups respectively; and $t_2$ and $t_3$ are identical with or different from each other, indicating 0 or 1; and a conjugate expressed by the following formula (III) are especially desirable.

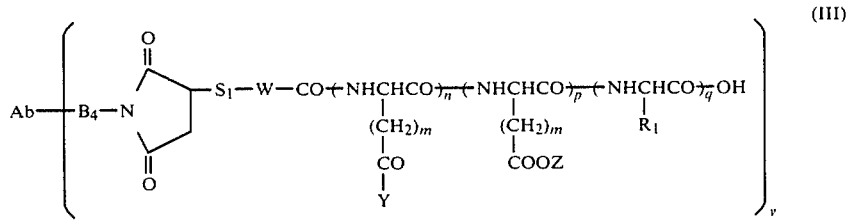

wherein Ab, $S_1$, W, $R_1$, Y, Z, m, n, p, q, and v are as defined with regard to formula (I); and $B_4$ indicates a divalent organic group.

In a conjugate having cytotoxicity expressed by formula (I), Y represents a residue of a cytotoxic substance which contains an amino group or an imino group in the molecule resulting from the reaction of such groups, as mentioned in the above. What is referred to as a cytotoxic substance in the present invention is one which directly exerts cytotoxic action on cells, or one which does not exert an cytotoxic action on cells directly but is convertible in vivo into a substance which exerts a cytotoxic action on cells. As examples of such cytotoxic substances, the following may be mentioned, but not to be limited to what is given below.

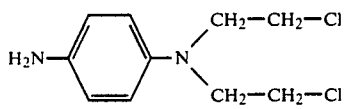

p-(N,N-bis(2-chloroethyl))phenylenediamine,

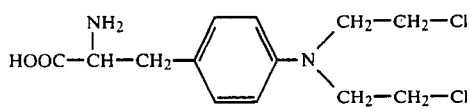

p-(bis(2-chloroethyl)amino)-L-phenylalanine(melphalan),

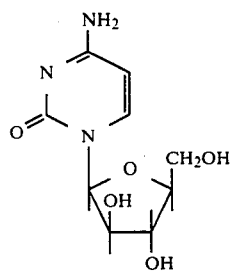

1-(β-D-arabinofuranosyl)cytosine or its monophosphate,

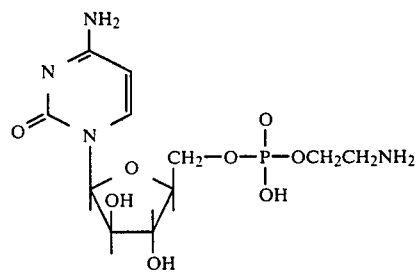

1-(5'-(2-aminoethylphosphoryl)-β-D-arabinofuranosyl)-cytosine,

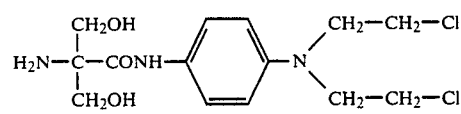

2-amino-N-(p-bis(2-chloroethyl)amino)phenyl-3-hydroxy-2-hydroxymethylpropionamide,

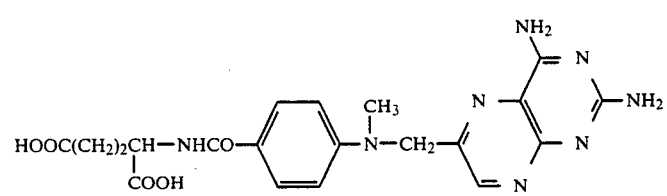

methotrexate,

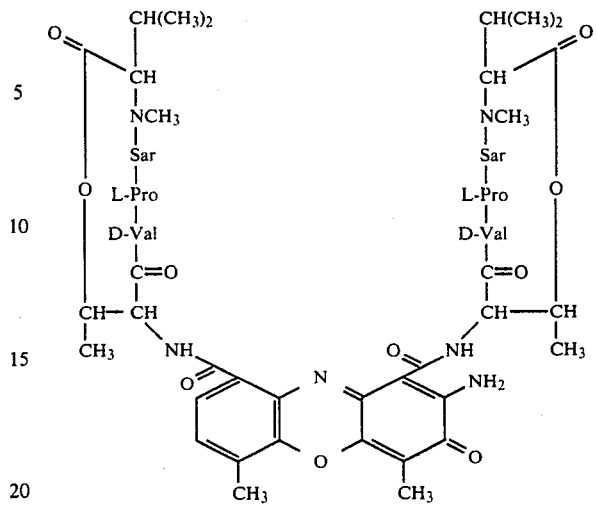

actinomycin D,

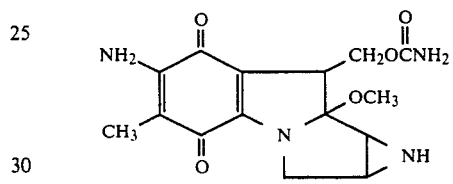

mitomycin C

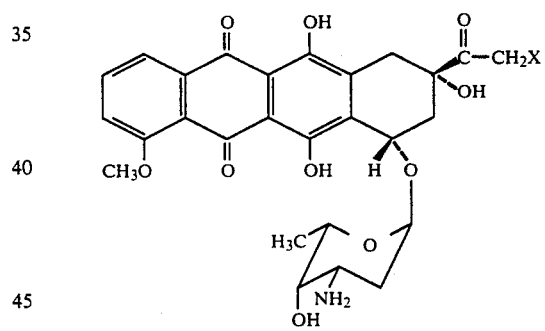

X=H, daunomycin,
X=OH, adriamycin.

Z indicates a hydrogen atom or a monovalent cation, and Na+, K+ and NH4+, for instance, may be mentioned.

W represents a divalent organic group and no limit may be placed on its kind so far as it is an inactive group that will not take part in the reaction to obtain a reactive polymer which is used as a material in the present invention. As these groups, such as unsubstituted alkylene group as one arising from 2-mercaptopropionic acid (—CH₂CH₂—) or such a substituted alkylene group as those arising from N—benzoylcysteine (—CH—CH₂—) and 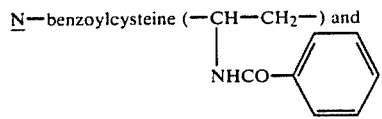

N—benzoylhomocysteine (—CH—CH₂—CH₂—) 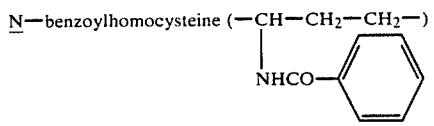

and such a phenylene group having no substituent group as one arising from 4-mercaptobenzoic acid ( 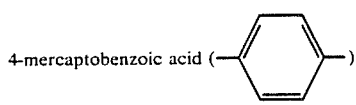 )

or an phenylene group having a substituent group, for instance, may be mentioned and an alkylene group having 1 to 4 carbon atoms is especially desirable. $R_1$ indicates a side chain at the α-position of α-amino acid or its derivative (excluding a group which has a carboxyl group) and, for instance, $R_1=H$ in case where α-amino acid is glycine, $R_1=CH_3$ in case where α-amino acid is alanine, $R_1=$

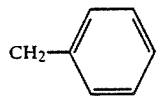

in case where α-amino acid is phenylalanine, and $R_1=CH_2OH$ in case where α-amino acid is serine. In the conjugate of formula (I), a structural unit comprising such α-amino acid does not participate in the binding of a cytotoxic substance but it is useful in the adjustment of the lipid-solubility and water-solubility of a conjugate or the affinity of a conjugate for a cell membrane. Therefore, in a case where the adjustment of the lipid-solubility and water-solubility of a conjugate is not especially needed, it is advantageous from the practical viewpoint to omit such a unit of α-amino (q=0 in formula (I)).

m indicates an intger 1 to 4 and should desirably be 1 or 2. Conjugates expressed by formula (I) include even such a conjugate that is mixedly composed of conjugates of m=1 and those of m=2.

n indicates the number of the structural units having a cytotoxic substance linked thereto, p indicates the number of the structural units not having a cytotoxic substance linked thereto, and q indicates the number of the units of α-amino acid having no carboxyl group on the side-chain (the side-chain may be modified), and the arrangements of these units in a polymer are discretionary. In formula (I), the structure is indicated as the arrangement of block polymerization, but this is not an absolute one, and a polymer obtained according to the ordinary method has a random arrangement. The respective numbers of structural units: n=5 to 1000, desirably 10 to 500; p=0 to 1500, desirably 0 to 500; and q=0 to 1500, desirably 0 to 500.

$S_1$ is a sulfur atom arising from a thiol group or an active disulfide group on the reactive polymer linked to a cytotoxic substance.

$B_1$ indicates a divalent organic group, and more particularly it indicates a residue arising from a cross-linking agent which has previously been introduced into an immunoglobulin or its fragment at the time of binding a reactive polymer having a cytotoxic substance linked thereto to the immunoglobulin or its fragment, or indicates a sulfur atom arising from a thiol group contained in the immunoglobulin or its fragment.

In case where $t_2=0$ in the aforementioned formula (II), $S_2$ is a sulfur atom arising from the immunoglobulin or its fragment and in case where $t_2=1$, $S_2$ is a sulfur atom introduced by the crosslinking agent. In case where $t_3=0$ in formula (II), the sulfur atom $S_1$ and $S_2$ directly bond to each other to form a disulfide group giving the conjugate expressed by the following formula (II-1).

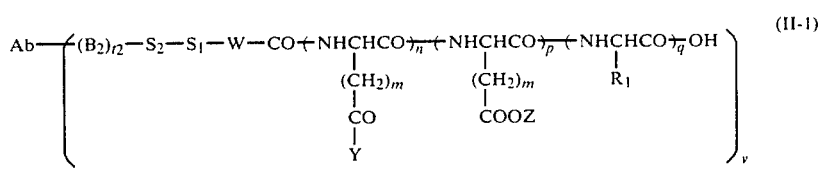

(wherein definitions of Ab, $S_1$, W, $R_1$, Y, Z, m, n, p, q, and v are the same as those given in case of formula (I); and $S_2$, $B_2$, and $t_2$ are as defined with regard to formula (II):)
while in case where $t_3=1$ in the aforementioned formula (II), the sulfur atoms $S_1$ and $S_2$ bond to each other through a divalent organic group $B_3$ giving the conjugates expressed by the following formula (II-2).

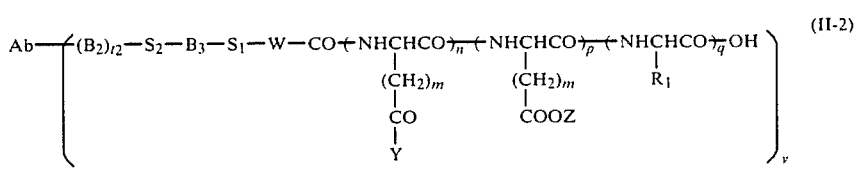

(wherein Ab, $S_1$, W, $R_1$, Y, Z, m, n, p, q, and v are as defined in case of formula (I) and $B_2$, $B_3$, and $t_2$ are as defined with regard to formula (II);)

In the above formulas (II) and (II-2), $B_3$ is a divalent organic group which arises either from a cross-linking agent having two functional groups that react with thiol groups, for example, a cross-linking agent expressed by the following formula (IX)

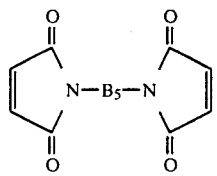 (IX)

wherein $B_5$ indicates a divalent organic group, or benzoquinone. $B_2$ is formula (II) is a divalent organic group which arises from the undermentioned cross-linking agents such as a cross-linking agent expressed by the following formula (X)

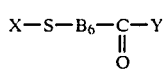 (X)

wherein definition of X is the same as that given in case of formula (V); $B_6$ is a divalent organic group; and Y represents an alcohol rest of an active ester:
a cross-linking agent expressed by the following formula (XI)

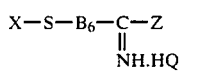 (XI)

wherein definition of X is the same as that given in case of formula (V) and $B_6$ is as defined with regard to formula (X); Z is an alcohol rest of imido ester; and Q indicates a halogen atom:
a cross-linking agent (2-iminothiolactone) expressed by the following formula (XII)

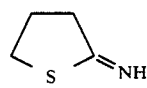 (XII)

and a cross-linking agent (N-acetylhomocysteine) expressed by the following formula (XIII)

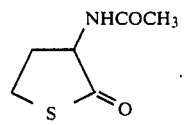 (XIII)

As concrete examples of a monovalent organic group, expressed by X, which is capable of forming an active disulfide group together with a linked sulfur atom, for instance, 2-pyridylthio group ( 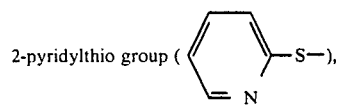

4-pyridylthio group (N 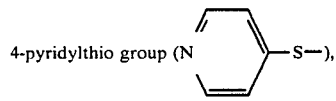

3-carboxy-4-nitrophenylthio group ($O_2N$— 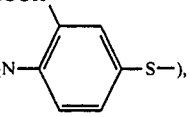 —S—), 4-carboxy-2-pyridylthio group (HOOC— —S—), $\underline{N}$—oxy-2-pyridylthio group ( —S— ), 2-nitrophenylthio group ( —S—), 4-nitro-2-pyridylthio group ($O_2N$— —S—), 2-benzothiazoylthio group ( —S), 2-benzoimidazoylthio group ( —S—), and $\underline{N}$—phenylamino-N'—phenyliminomethylthio group

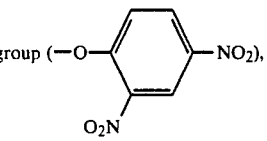

may be mentioned.

Though no specific limit is placed upon said divalent organic group expressed by $B_5$ or $B_6$ so far as it is chemically inert, it may be freely chosen from among alkylene groups which have or have not branching, phenylene groups, etc. in general. By way of concrete example of the alcohol rest of an active ester expressed by Y, 2,4-dinitrophenoxy group (—O— —$NO_2$), succinimidoxy group 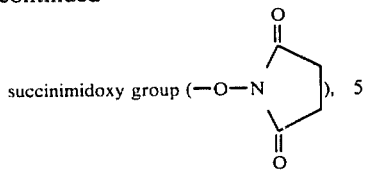, etc. may be mentioned. As an example of the alcohol rest of imidoester expressed by Z, methoxy group, ethoxy group, etc. may be mentioned. As an example of the halogen atom expressed by Q, chlorine atom, bromine atom, etc. may be mentioned.

To mention concrete examples of said cross-linking agent, there are cross-linking agents expessed by formula (IX) such as N,N'—(1,2-phenylene)dimaleimide 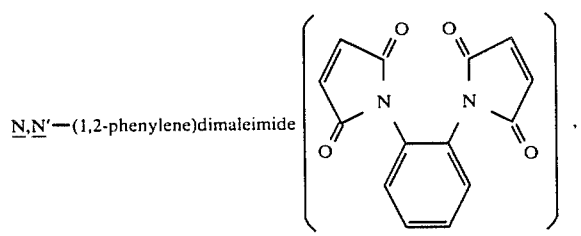, N,N'—(1,4-phenylene)dimaleimide 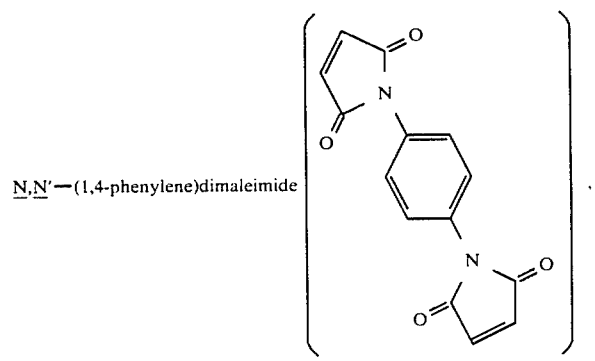, 4,4'-bis(maleoylamino)azobenzene 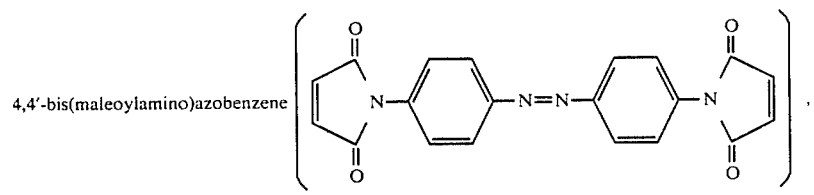, bis(N—maleimidomethyl)ether 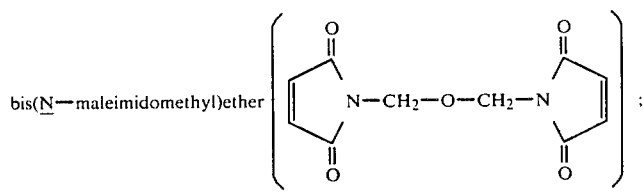;

cross-linking agents expressed by formula (X) such as N-succinimidyl 3-(2-pyridyldithio)propionate and N-succinimidyl 3-(2,4-dinitrophenoxy)butylate; and cross-linking agents expressed by formula (XI) such as methyl 3-(2-pyridyldithio)propionimidate hydrochloride.

In the aforementioned formula (III), $B_4$ is a divalent organic group arising from a cross-linking agent having a maleimide group, expressed by the following formula (XIV),

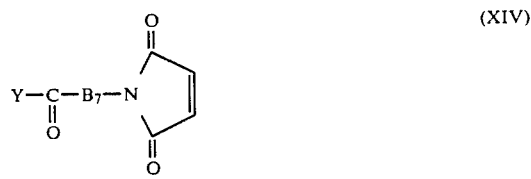 (XIV)

wherein Y has the definition given earlier in formula (X) and $B_7$ is a divalent organic group.

The divalent organic group expressed by $B_7$ has no specific limit placed upon it, so far as it is chemically inert; however, it may be freely chosen from among alkylene groups which have or have not branching, phelylene groups, etc.

As concrete examples of the cross-linking agent expressed by formula (XIV), meta-(N-maleimido)benzoic acid

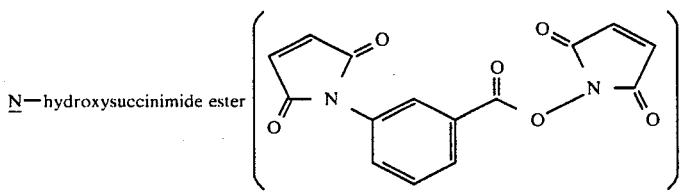

N—hydroxysuccinimide ester meta-(N-maleimido)benzoic acid 2,4-dinitrophenylester, β-(N-maleimido)propionic acid N-hydroxysuccinimide ester, etc. may be mentioned.

The conjugate having cytotoxicity of the present invention can be prepared by covalently linking a reactive polymer carrying a cytotoxic substance linked thereto to an immunoglobulin or its fragment. More particularly, of the conjugates having cytotoxicity of the present invention, a conjugate expressed by formula (II-1) can be prepared by reacting a reactive polymer, which has a cytotoxic substance linked thereto and also has an active disulfide group at the terminal of its molecule, expressed by the following formula (V)

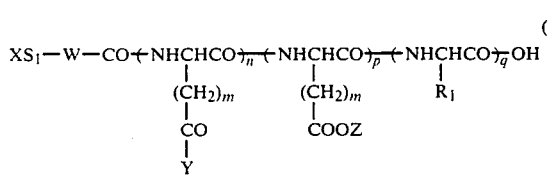
(V)

wherein definitions of $S_1$, W, $R_1$, Y, Z, m, n, p, and q are the same as those given in case of formula (I); and X indicates a group which is capable of forming an active disulfide linkage with a neighboring sulfur atom:

with an immunoglobulin or its fragment expressed by the following formula (IV) having a generated or introduced thiol group $$Ab—(B_2)_{t_2}—S_2H)_{v'} \qquad (IV)$$

wherein Ab is as defined with regard to formula (I); definitions of $S_2$, $B_2$, and $t_2$ are the same as those given in case of formula (II); and v' is an integer 1 to 10:

or by reacting a reactive polymer expressed by the following formula (VII), which has a cytotoxic substance linked thereto and also has a thiol group at the terminal of its molecule,

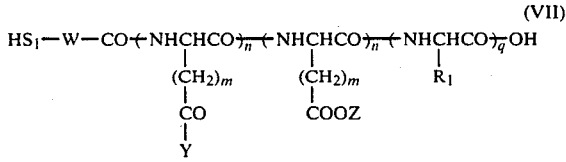
(VII)

wherein $S_1$, w, $R_1$, Y, m, n, p, and q are as defined with regard to formula (I):

with an immunoglobulin or its fragment expressed by the following formula (VI) having an induced or introduced active disulfide group $$Ab—(B_2)_{t_2}—S_2X)_{v'} \qquad (VI)$$

where Ab is as defined with regard to formula (I); $S_2$, $B_2$, and $t_2$ are as defined in case of formula (II); v' is as defined in case of formula (IV); and X is as defined with regard to formula (V).

In the aforementioned formula (IV), when $t_2 \ne 0$, the immunoglobulin or its fragment expressed by formula (IV) is either an immunoglobulin or its fragment having thiol group(s) of its own as represented by monomeric IgMs obtained from IgM and Fab', or an immunoglobulin or its fragment having thiol group(s) generated from the disulfide group. The immunoglobulin or its fragment expressed by formula (IV), wherein $t_2=1$, having thiol group(s) can be prepared either by allowing an immunoglobulin or its fragment to react with a cross-linking agent expressed by said formula (X) or (XI), followed by the reduction reaction in which thiol group(s) are generated from the introduced active disulfide group, or by allowing an immunoglobulin or its fragment to react with a cross-linking expressed by said formula (XII) or (XIII).

In case where $t_2=0$ in the aforementioned formula (VI), the immunoglobulin or its fragment having such an active disulfide group can be prepared by subjecting an immunoglobulin or its fragment having its own or generated thiol group to the action of an active disulfide group introducing agent.

As the active disulfide compounds which can be used for the abovementioned purpose,

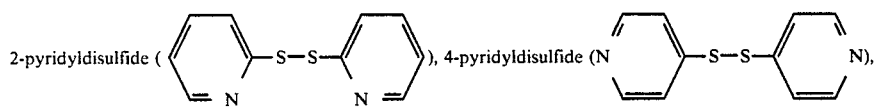

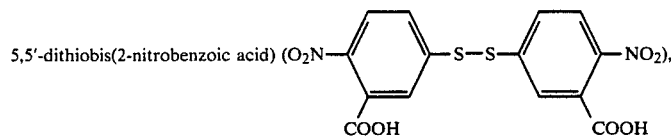

-continued

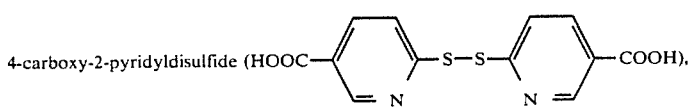
4-carboxy-2-pyridyldisulfide (HOOC—⟨ ⟩—S—S—⟨ ⟩—COOH),

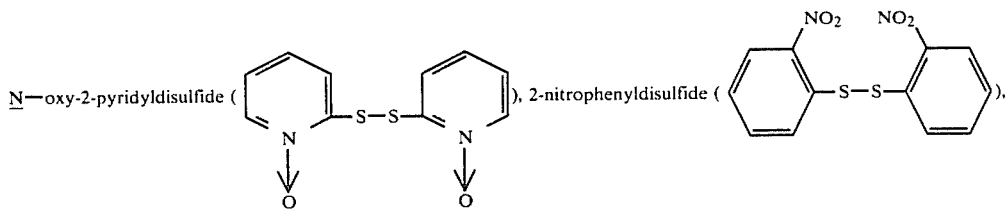
N—oxy-2-pyridyldisulfide ( ), 2-nitrophenyldisulfide ( ),

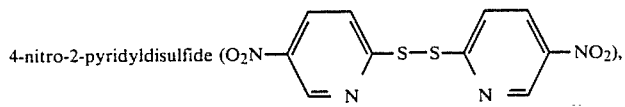
4-nitro-2-pyridyldisulfide (O₂N— —S—S— —NO₂),

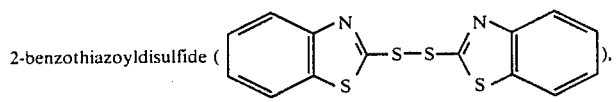
2-benzothiazoyldisulfide ( ),

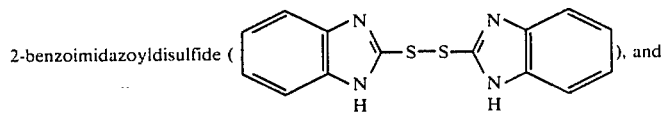
2-benzoimidazoyldisulfide ( ), and

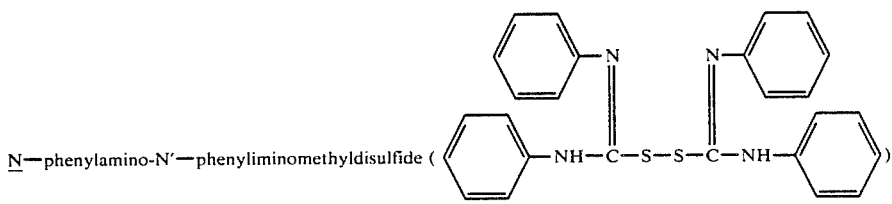
N—phenylamino-N'—phenyliminomethyldisulfide ( )

may be mentioned.

When the disulfide linkage at the hinge part of the aforementioned F(ab')₂ is broken by sulfonation with the use of sulfite ion, Fab' having an S-sulfo group (—S—SO₃⁻) in the molecule can be obtained. This Fab' favorably reacts with a reactive polymer expressed by formula (VII) having a cytotoxic substance linked thereto to form a conjugate having cytotoxicity expressed by formula (II-1).

A process for the preparation of a reactive polymer expressed by formula (V) or formula (VII) having a cytotoxic substance linked thereto will be described later.

Of the conjugates having cytotoxicity of the present invention, a conjugate expressed by formula (II-2) can be prepared by binding a reactive polymer expressed by said formula (VII) having a cytotoxic substance linked thereto to an immunoglobulin or its fragment expressed by said formula (IV) having a generated or introduced thiol group with the use of a cross-linking agent having 2 functional groups which are able to react with thiol groups. It is desirable to carry out the abovementioned process in a two-step reaction. In the first step, either an immunoglobulin or its fragment expressed by formula (VI) having a generated or introduced thiol group or a reactive polymer expressed by formula (VII) having a cytotoxic substance linked thereto is allowed to react with an excess of the cross-linking agent, for instance, expressed by formula (IX), followed by the purification of the obtained intermediate product. In the second step, thus obtained intermediate product is made to react with the other of the proteins. By following the abovementioned reaction procedures, the desired conjugate having cytotoxicity expressed by formula (II-2) can be obtained.

Further, of the conuugates having cytotoxicity of the present invention, a conjugate expressed by formula (III) can be prepared, for instance, by reacting a reactive polymer expressed by the above-mentioned formula (VII) having a cytotoxic substance linked thereto with an immunoglobulin or its fragment expressed by the following formula (VIII) having an introduced maleimide group

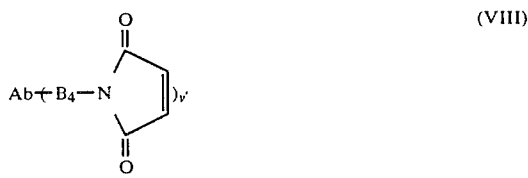
(VIII)

wherein a definition of Ab in the same as that given in case of formula (I); v' has the meaning given in case of formula (IV); and B₄ is as defined with regard to formula (III).

The immunoglobulin or its fragment expressed by said formula (VIII) having an introduced maleimide group can be prepared, for instance, by making an immunoglobulin or its fragment react with a cross-linking agent expressed by said formula (XIV) having a maleimide group.

Next, an explanation will be made hereunder as to the process of preparing a reactive polymer expressed by said formula (V) or formula (VII) having a cytotoxic substance linked thereto which is to be used as a material in the present invention. There are various processes for the preparation of such reactive polymer carrying a cytotoxic substance and one of them will be described as an example in the following.

An explanation will be given below citing one example of the process for the preparation of a reactive polymer expressed by formula (V) or formula (VII) having a cytotoxic substance linked thereto, wherein $n=2$, $q=0$, $w=-CH_2CH_2CO-$,

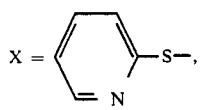

Y=daunomycin residue, and Z=Na. Firstly, poly-L-glutamic acid (sodium salt) whith is a hydrophilic polymer, is allowed to react with N-succinimidyl 3-(2-pyridyldithio)propionate

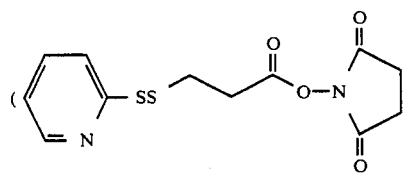

in an aqueous solution at room temperature to have 3-(2-pyridyldithio)propionyl group introduced to the amino terminal of poly-L-glutamic acid as shown in the following chemical formulas:

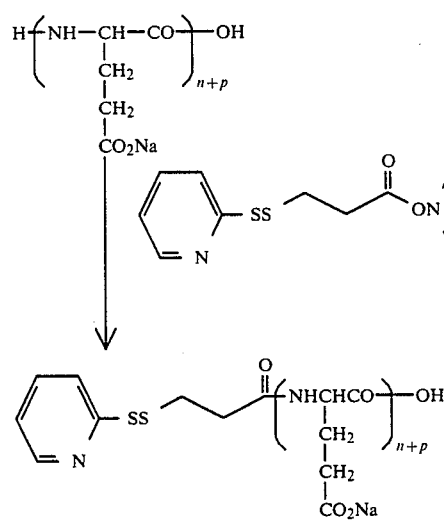

Then daunomycin is made to react with poly-L-glutamic acid (sodium salt), which has an active disulfide group at its terminal, in an aqueous solution at room temperature in the presence of water-soluble carbodiimide, thus obtaining a reactive polymer of formula (V) having a reactive disulfide group at the terminal as follows

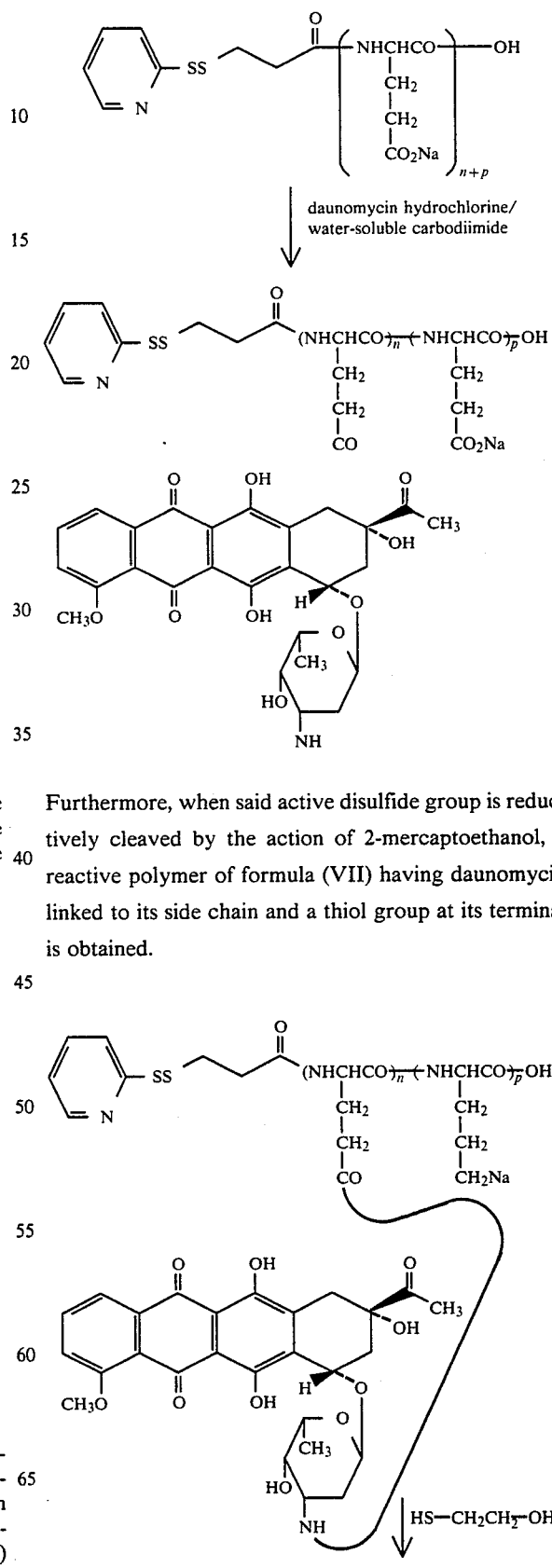

Furthermore, when said active disulfide group is reductively cleaved by the action of 2-mercaptoethanol, a reactive polymer of formula (VII) having daunomycin linked to its side chain and a thiol group at its terminal is obtained.

-continued

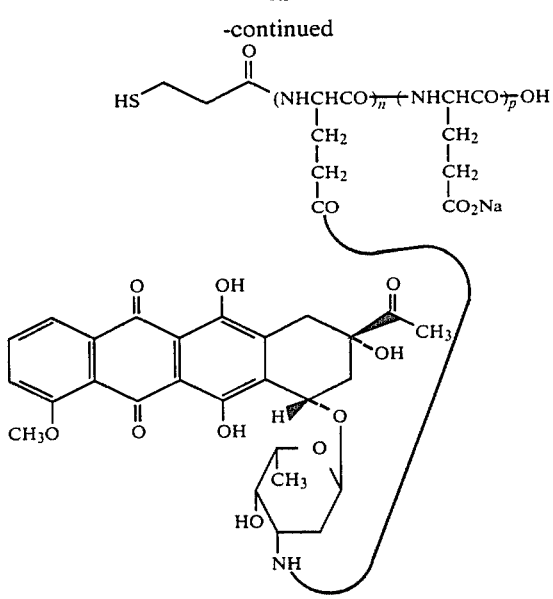

A process for the preparation of a conjugate having cytotoxicity is explained by example in the following.

(1) A method in which a reactive polymer expressed by formula (V) having a cytotoxic substance linked thereto and has an active disulfide group at the terminal of its molecule is allowed to react with an immunoglobulin or its fragment expressed by formula (IV) having a generated or introduced thiol group, or in which a reactive polymer expressed by formula (VII) having a cytotoxic substance linked thereto is made to react with an immunoglobulin or its fragment expressed by formula (VI) having an active disulfide group.

In the abovementioned methods, it is desirable to use 0.3 to 20 moles of a reactive polymer expressed by formula (V) having an active difulfide group and a cytotoxic substance linked thereto to 1 mole of an immunoglobulin or its fragment expressed by formula (IV) having a thiol group. The reaction can be carried out by mixing the protein and the polymer in a buffer solution adjusted to pH 6 to 10 in such a way as to have the total concentration of 0.5 to 100 mg/ml (more desirably 1 to 20 mg/ml), followed either by allowing the reaction mixture to stand at 0° to 60° C., or by dialyzing the reaction mixture against a buffer having the same pH value as the reaction mixture. The reaction time varies depending upon the reaction scale and conditions; however, it usually ranges between 4 hours and 3 days. The separation of the obtained conjugate having cytotoxicity from the reaction mixture and its purification can be effected according to the ordinary procedures, for instance, by means of dialysis and gel filtration chromatography.

(2) A method in which an immunoglobulin or its fragment expressed by formula (IV) having a thiol group and a reactive polymer expressed by formula (VII) having a cytotoxic substance linked thereto and also a thiol group at the terminal of its molecula are bonded to each other by use of a cross-linking agent of formula (IX) which is able to react with the thiol groups of both the protein and the polymer.

In the above method, the reaction can be carried out by simultaneously bringing an immunoglobulin or its fragment having a thiol group, a cross-linking agent, and a reactive polymer having a cytotoxic substance linked thereto and a thiol group into direct contact with each other; however, it is desirable to carry on the process first by making a protein react with a cross-linking agent and then by allowing the reaction product to react with a polymer. In this latter case, 0.8 to 50 moles of a cross-linking agent and 0.8 to 10 moles of a protein or a reactive polymer are used preferably to 1 mole of the protein or a reactive polymer which is to react with the protein or the reactive polymer. The reaction is initiated by adding a cross-linking agent, which is dissolved in a small quantity of such a solvent as N,N'-dimethylformamide, dimethyl sulfoxide, 1,2-dimethoxyethane, methanol, ethanol, acetone, etc., to a buffer solution with the pH adjusted to 6 to 10 containing an immunoglobulin or its fragment having a thiol group or a reactive polymer having a cytotoxic substance linked thereto (the solution is to be prepared to have the protein and polymer concentration of 0.5 to 100 mg/ml preferably, and 1 to 20 mg/ml more preferably) at at temperature ranging from 0° to 60° C. with stirring. After the removal of the cross-linking agent remaining not yet reacted by means of dialysis or gel filtration chromatography, a buffer solution of pH 6 to 10 containing the other protein or the polymer (the preferable range of protein and polymer concentration is the same as that mentioned above) is added to the reaction mixture to resume the reaction at 0° to 60° C. The separation of thus obtained conjugate having cytotoxicity from the reaction mixture and its purification can be effected according to an ordinary method such as gel filtration chromatography.

(3) A method in which a reactive polymer expressed by formula (VII) having a cytotoxic substance linked thereto and an immunoglobulin or its fragment expressed by formula (VIII) having an introduced maleimide group are made to react with each other.

In this method, it is desirable to use 0.3 to 10 moles of a reactive polymer expressed by formula (VII) having a cytotoxic substance linked thereto to 1 mole of an immunoglobulin or its fragment expressed by formula (VIII) having an introduced maleimide group. The reaction can be carried out by mixing the protein or the polymer in a buffer solution with its pH value adjusted to 6 to 10 in such a way as to obtain the total protein and polymer concentration of 0.5 to 100 mg/ml (more preferably 1 to 20 mg/ml) and then by allowing the reaction mixture to stand at 0° to 60° C. The time reqired for completing the reaction varies depending upon the reaction scale and conditions but it generally ranges from 4 hours to 3 days. The obtained conjugate having cytotoxicity is separated from the reaction mixture and purified according to the ordinary method such as dialysis and gel filtration column chromatography.

The present invention is described in detail by the following examples and referential example.

REFERENTIAL EXAMPLE (a) Preparation of anti mouse leukemia L 1210 IgG

An emulsion prepared from $1 \times 10^6$ mouse leukemia L 1210 cells and Freund's complete adjuvant was intravenously injected into a rabbit. Thereafter, $1 \times 10^6$ L 1210 cells, together with the adjuvant, were further subcutaneously injected three times at intervals of one week, and the rabbit was bled eight days after the day of final injection. The portions of blood thus obtained were pooled and mixed and the serum was separated therefrom and heated at 56° C. for 30 minutes for inactivation. 200 ml of saturated aqueous solution of ammonium sulfate was added to 200 ml of thus obtained anti-L 1210 antiserum and the resulting precipitate was separated by means of centrifugation. The precipitate thus separated was dissolved in 50 ml of 0.01M phosphate buffer (pH 7.6) and was further dialyzed thoroughly against the same buffer. The dialyzate was subjected to DEAE cellulose column chromatography (column size 3 cm×94 cm) equilibrated with the same buffer to obtain a solution containing anti-L 1210 IgG as an unadsorbed fraction.

(b) Separation of fragment F(ab')₂ from immunoglobulin 1.2 g of anti-L 1210 IgG obtained in the preceding (a) was dissolved in 40 ml of 0.1M acetate buffer (pH 4.5), to which 24 mg of pepsin was added to effect peptic digestion at 37° C. for about 18 hours. The digestion product was subjected to Sephadex G 200 column chromatography (column size 3.5 cm×140 cm) over saline to take out a protein eluted at molecular weight of about 100,000 as a pure fragment F(ab')₂.

(c) Preparation of fragment Fab'

0.02 ml of an aqueous solution of 150 mM 2-mercaptoethanol was added to 2.0 ml of 0.01M tris hydrochloride—0.14M sodium chloride—2 mM EDTA solution (pH 8.3) containing 18.4 mg of fragment F(ab')₂ obtained in the preceding (b) and the mixture was subjected to the reduction reaction at 37° C. for 1 hour. After the reaction was over, the solution was put to Sephadex G-25 column chromatography (column size 1.0 cm×20 cm) equilibrated with 5 mM acetate buffer—0.14M sodium chloride-1 mM EDTA solution (pH 5.5) (hereinafter referred to as ANE buffer) to remove 2-mercaptoethanol, thus giving fragment Fab' having 1 thiol group.

(d) Purification of IgM 100 ml of saturated ammonium sulfate solution was added to 100 ml of anti-L 1210 antiserum obtained according to the aforesaid (a) and the resulted precipitate was separated by centrifugation. The obtained precipitate was dissolved in an aqueous solution of 0.9% potassium chloride. After the caused insoluble substance was removed by centrifugation, the solution was put to Sephadex G-200 column chromatography (column size 2.2 cm×102 cm) equilibrated with 0.9% sodium chloride solution to obtain a fraction of IgM at the first peak. Saturated ammonium sulfate was added to the obtained fraction of IgM, equal in volume to each other. After the resulting precipitate was separated by centrifugation, it was dissolved in a small amount of 0.9% sodium chloride solution and the solution was dialyzed thoroughly against the same 0.9% sodium chloride solution.

(e) Preparation of IgMs 1.8 ml of rabbit IgM dissolved in an aqueous solution of 0.9% sodium chloride (0.5 mg/ml) and 0.2 ml of 0.2M cysteine dissolved in 1M tris. hydrochloride buffer (pH 8.6) were mixed together. After the mixture was reduced at room temperature for 16 hours, excess cycteine was removed by gel filtration (buffer A used as a solvent) with the use of Sephadex G-25 (column size 0.8 cm×43 cm).

(f) Preparation of immunoglobulin specific to α-fetoprotein of rat

An emulsion comprising 1 mg of purified α-fetoprotein (hereinafter referred to as AFP) of rat and Freund's complete adjuvant was subcutaneously injected to a horse once a week to make the horse hyperimmunized. Blood was drawn from this horse and serum was separated. The obtained serum was fractionated with ammonium sulfate and purified by affinity chromatography on a column of Sepharose 6B and gel filtration by Sephadex G-200, to give a pure horse immunoglobulin of anti-rat AFP.

(g) Preparation of poly-L-glutamic acid having daunomycin linked to side chain and containing 2-pyridyldithio group or thiol group at terminal

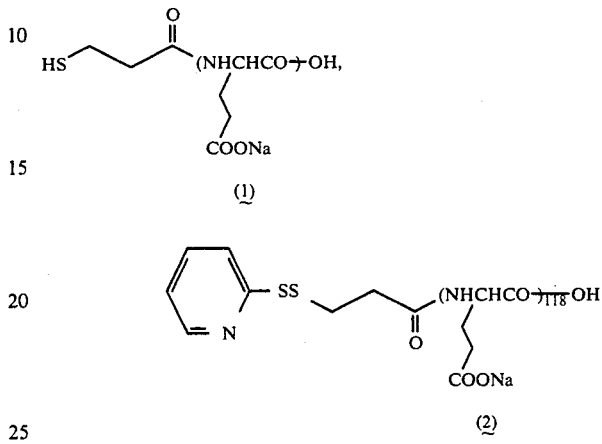

An ethanol solution (6 ml) containing 68.8 mg of N-succinimidyl 3-(2-pyridyldithio)propionate (hereinafter referred to as SPDP) was added to a solution of 0.1M sodium phosphate buffer (pH 7.5, 15 ml) containing 226.5 mg of sodium salt of poly-L-glutamic acid dissolved therein with stirring in two portions and the mixture was allowed to react at room temperature for 1.5 hour. The reaction solution was put in a cellophane dialysis tube and dialized against 0.01M phosphate buffer (pH 7.5) at 4° C. for 2 days to remove the low molecular weight substance. A solution of 17 mg of dithiothreitol in 2.0 ml of 0.1M sodium phosphate buffer (pH 6.0) was added to the recovered solution (50 ml) and the mixture was made to react at room temperature for 80 minutes. The reaction solution was then made acidic with hydrochloric acid and the resulting precipitate was separated by centrifugation. The obtained precipitate of poly-L-glutamin acid (containing both poly-L-glutamic acid having a thiol group at the terminal and poly-L-glutamic acid having no thiol group) was washed with 0.01N HCl.

On the other hand, 15 ml of Thiopropyl Sepharose ® 6B gel (manufactured by Pharmacia Co., Ltd.) was dispersed in 40 ml of 0.1M sodium phosphate (pH 6.0)—1 mM ethylene diaminetetraacetic acid (hereinafter referred to sa EDTA) (pH 6.0) buffer solution. A solution prepared by dissolving the poly-L-glutamic acid obtained in the above in 10 ml of the same buffer solution as the above was added to thus prepared dispersion and the mixture was stirred slowly at room temperature in an atmosphere of nitrogen overnight. In this reaction, poly-L-glutamic acid having a thiol group at its terminal was linked to the polymer. Thereafter, the polymer was separated by filtration and washed thoroughly with 0.01M phsophate buffer (pH 7.5).

Thus obtained polymer was dispersed in 50 ml of 0.1M tris.HCl—1 mM EDTA (pH 8.5) buffer, to which 1.17 g of 2-mercaptoethanol was added and the mixture was stirred slowly at room temperature in an atmosphere of nitrogen for 10 hours. This reaction liberated the poly-L-glutamic acid (1) having a thiol group at its terminal from the polymer.

The polymer was separated by filtration and washed thoroughly with 0.01M tris.HCl—0.1 mM EDTA (pH 8.5) buffer. Then the combined solution of the filtrate and the washings was adjusted to pH 1.8 while being cooled with ice and the resulting precipitate of poly-L-glutamic acid having a thiol group at its terminal was separated by centrifugation.

The obtained precipitate was again dissolved in 1 ml of 0.4M sodium phosphate—1 mM EDTA (pH 7.5) buffer. The solution was added to a solution which was prepared by adding an ethanol (4 ml) solution containing 23 mg of 2-pyridyldisulfide (hereinafter referred to as 2-PDS) to 10 ml of 0.1M sodium phosphate—1 mM EDTA (pH 6.0) buffer and the mixture was made to react at room temperature for 30 minutes (wherein poly-L-glutamic acid was made to have an active disulfide group at its terminal). The reaction solution was then put in a cellophane tube and dialyzed against 0.01M sodium phosphate (pH 7.5) buffer for 6 hours and further against pure water for 1 day. The recovered solution was reduced to 30 ml under reduced pressure and then lyophilized to give 35.4 mg of poly-L-glutamic acid (sodium salt) having an introduced 2-pyridyldithio group at its terminal (2) in the form of a flocculated solid (yield by weight 15.6%).

Determination of 2-pyridyldithio group at the terminal (3)

A fixed quantity of the sample was weighted out accurately (1.895 mg) and dissolved in 3.00 ml of 0.1M sodium phosphate buffer (pH 7.2). A small piece of dithiothreitol was added to the solution and the absorbance due to the liberated 2-mercaptopyridine (at 343 nm, (molecular absorptivity) $\epsilon = 8080$) was measured (A=0.286). The terminal group in the accurately weighed sample was determined to be $0.1062\mu$ mole. Accordingly, the molecular weight of poly-L-glutamic acid molecule containing terminal active disulfide in the sample was determined to be 17,800 and the number of units of glutamic acid (sodium salt) in said molecule was calculated to be 118 based on the mass number of 151 per unit.

Next, 25 mg ($1.40\mu$ mole) of poly-L-glutamic acid (sodium salt) containing a 2-pyridyldithio group at its terminal (molecular weight 17,800) was dissolved in 6 ml of 5% saline water, to which 11.2 mg of daunomycin hydrochloride salt and 38.1 mg of 1-ethyl-3-(3-dimethylaminopropyl)carbodiimide hydrochloride salt (hereinafter referred to as EDCI.HCl) were added. The mixture was made to react at room temperature overnight. The reaction solution was placed in a cellophane tube and dialyzed thoroughly against water at 4° C. The recovered solution was concentrated to 10.5 ml under reduced pressure to give an aqueous solution of the desired PLGA (sodium salt) (4) containing 2-pyridylthio group at the terminal and having daunomycin on the side chain linked thereto. The quantity of linked daunomycin was determined from the absorbance obtained at 490 nm and the terminal group was determined from the absorbance at 343 nm due to 2-mercaptopyridine liberated by addition of dithiothreitol as in the case of preceding (g) to give the following result. The quantity of daunomycin was $1.16 \times 10^{-5}$ moles, the quantity of the terminal groups $1.36 \times 10^{-6}$, the average number of daunomycin linked to PLGA chain 8.53; the recovery of PLGA 97% respectively.

EXAMPLE 1

1-(a) Preparation immunoglobulin having introduced maleimide group 0.1 ml of N,N-dimethylformamide (hereinafter referred to as DMF) containing 1.57 mg of N-hydroxysuccinimidyl-m-maleimidobenzoate (hereinafter referred to as SMB) dissolved therein was added to 1.60 ml of 0.1M phosphate buffer (pH 6.5) containing 37.4 mg of anti AFP horse immunoglobulin (IgG) obtained according to the method of Referential Example, (f), and were allowed to react at room temperature for 30 minutes. Fifty $\mu$l of 1M tris.hydrochloric acid buffer (pH 6.9) was added to the above solution and the reaction was terminated. Then the reaction solution was made to pass through the column (0.8 cm × 42 cm) of Sephadex G-25 (5 mM acetate buffer—0.14M sodium chloride (hereinafter referred to as NaCl)—1 mM ethylenediaminetetraacetic acid (hereinafter referred to as EDTA) (pH 5.5)) to remove the excess sample drug, thus giving 2.96 ml of a solution containing anti AFP horse IgG having introduced maelimide groups.

1-(b) Preparation of conjugate having cytotoxicity (1-3) by reacting immunoglobulin (1-1) having introduced maleimide groups with poly-L-glutamate (1-2) containing thiol group at terminal and having daunomycin linked to side chain

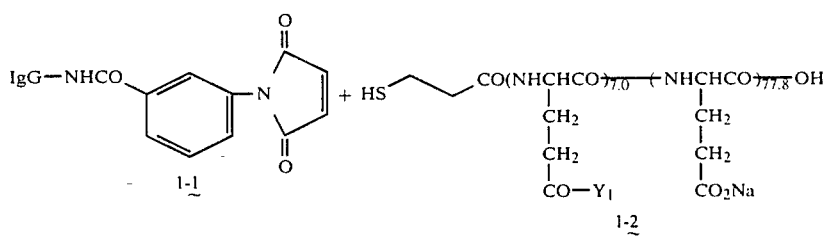

-continued

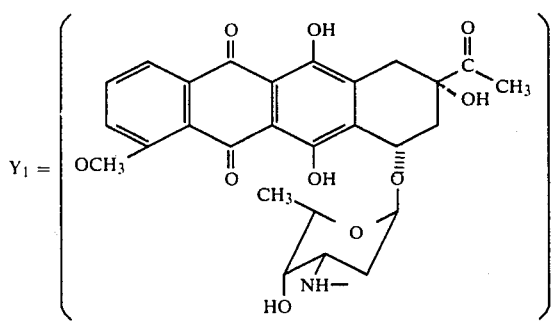

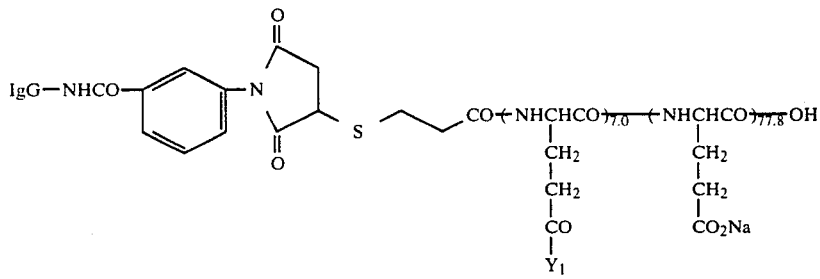

1-3

5.05 ml of 5 mM acetic acid buffer—0.14M NaCl—1 mM EDTA (pH 5.5)) solution containing poly-L-glutamic acid (sodium salt) (1-2), which contained a thiol group at its terminal and had daunomycin linked to its side chain (terminal thiol group equivalent to $3.88 \times 10^{-7}$ mole/ml), obtained according to Referential Example, (g), and 2.0 ml of 0.5M acetic acid buffer (pH 6.5) were added to 2.96 ml of a solution (5 mM acetic acid buffer—0.14M NaCl—1 mM EDTA (pH 5.5) containing 29.4 mg of IgG (1-1) having an m-maleimidobenzoyl group introduced thereinto obtained according to the preceding 1-(a), and the mixture was made to react at 4° C. overnight. The equivalent volume of 50% saturated ammonium sulfate solution was added and 5 minutes later the precipitate resulted was separated by centrifugation. After the obtained precipitate was dissolved in 4 ml of 10 mM phosphoric acid buffer—0.14M NaCl (pH 7.4), the solution was thoroughly dialyzed against the same buffer.

1-(c) Cytotoxicity of conjugate (1-3) against rat kepatoma AH 66 cells

The cytotoxicity of the conjugate 1-3 obtained according to the preceding 1-(b) against the target AH 66 cells was examined.

A total of 0.2 ml of Eagle MEM culture medium containing 10% horse serum, $1 \times 10^3$ AH 66 cells, and test sample was placed in a well of a 96-hole culture plate and the culture was carried out at 37° C. in an atmosphere of 5% $CO_2$ for 48 hours. When the culture was over, the viable cells were counted by dye exclusion with Trypan Blue. The culture was carried out in three groups and their average values are shown. The result is shown in Table 1.

TABLE 1

| No. | Test sample | Drug concentration (µg/ml) Immuno-globulin | Drug concentration (µg/ml) Dauno-mycin | Number of viable cells after 48-hour culture $\times 10^{-3}$/ml |
|---|---|---|---|---|
| 1 | No drug added | — | — | 17.2 ± 1.2 |

TABLE 1-continued

| No. | Test sample | Drug concentration (µg/ml) Immuno-globulin | Drug concentration (µg/ml) Dauno-mycin | Number of viable cells after 48-hour culture $\times 10^{-3}$/ml |
|---|---|---|---|---|
| 2 | Nonimmunized horse immunoglobulin | 0.4 | — | 16.4 ± 1.3 |
|  |  | 4 | — | 16.0 ± 2.0 |
|  |  | 40 | — | 15.9 ± 1.4 |
|  |  | 400 | — | 16.4 ± 1.3 |
| 3 | Anti rat AFP horse immunoglobulin | 0.4 | — | 14.8 ± 0.8 |
|  |  | 4 | — | 12.6 ± 1.5 |
|  |  | 40 | — | 8.8 ± 1.7 |
|  |  | 400 | — | 2.3 ± 0.4 |
| 4 | Daunomycin | — | 0.1 | 6.4 ± 0.7 |
|  |  | — | 1 | 1.7 ± 0.2 |
|  |  | — | 10 | 0.2 ± 0.04 |
|  |  | — | 100 | 0 |
| 5 | Conjugate of poly-L-glutamic acid and daunomycin | — | 0.1 | 9.1 ± 0.7 |
|  |  | — | 1 | 3.2 ± 0.4 |
|  |  | — | 10 | 0.39 ± 0.04 |
|  |  | — | 100 | 0 |
| 6 | Conjugate of nonimmunized horse immunoglobulin-poly-L-glutamic acid-daunomycin | 0.4 | 0.1 | 10.4 ± 1.6 |
|  |  | 4 | 1 | 4.0 ± 0.36 |
|  |  | 40 | 10 | 0.68 ± 0.08 |
|  |  | 400 | 100 | 0.097 ± 0.019 |
| 7 | Conjugate of anti AFP horse immunoglobulin-poly-L-glutamic acid-daunomycin (Conjugate 1-3) | 0.4 | 0.1 | 4.0 ± 0.55 |
|  |  | 4 | 1 | 0.67 ± 0.66 |
|  |  | 40 | 10 | 0.093 ± 0.014 |
|  |  | 400 | 100 | 0 |

It is confirmed from Table 1 that the conjugate having cytotoxicity of the present invention (No. 7) has a remarkable cytotoxicity against rat hepatoma AH 66 cells.

EXAMPLE 2

2-(a) Preparation of IgG having introduced active thiol group 100

100 µl of 5 mM ethanol solution of N-succinimidyl 3-(2-pyridyldithio)propionate was added to 4 ml of 0.1M sodium phosphate buffer (containing 0.1M sodium chloride, pH 7.5) containing 20 mg of IgG obtained according to Referential Example, (a), and the mixture was allowed to react at room temperature with occasional stirring for 30 minutes. Then the reaction solution was made to pass through a column (0.8 cm×40 cm) of Sephadex G-25 equilibrated with the abovementioned buffer to remove the excess reagent, thus obtaining IgG containing 1.9 3-(2-pyridyl)dithiopropionyl groups per molecule.

2-(b) Preparation of conjugate having cytotoxicity (2-3) by reaction between dithiopropionyl IgG (2-1) and poly-L-glutamate having a thiol group and having mitomycin C linked thereto (2-2)

the viable cells were counted by dye exclusion with Trypan Blue.

The result, given in Table 2, shows that the hybrid (2-3) displayed a remarkable effect in prohibiting the proliferation of the target L 1210 cells depending on the concentrations. The culture was carried out in two groups and the values shown are their averages.

TABLE 2

| Mitomycin concentration in conjugate (2-3) (μm) | Number of viable cells after 48-hour culture × $10^{-4}$/ml |
|---|---|
| 0 | 26.0 |
| 0.1 | 23.8 |
| 1 | 2.8 |

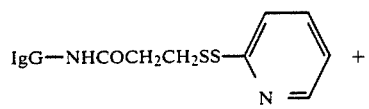

(2-1)

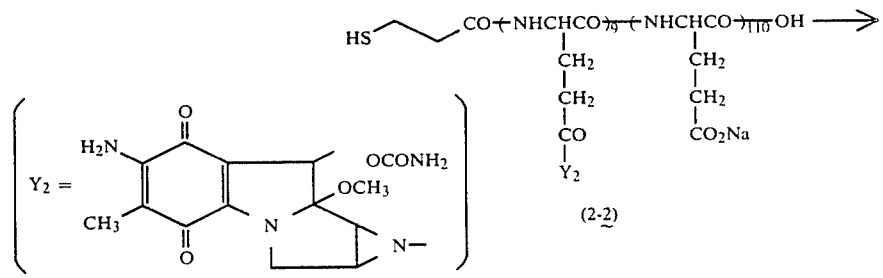

(2-2)

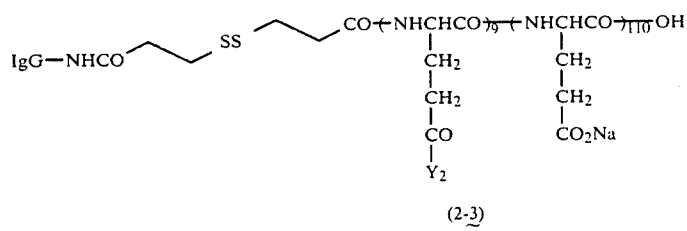

(2-3)

40 μl of a solution of poly-L-glutamate having a thiol group and having mitomycin C linked thereto (2-2) (terminal SH equivalence 5.3×$10^{-7}$ mole/ml) was added to 2.5 ml of a solution containing 2.8 mg of 3-(2-pyridyl)dithiopionyl IgG (2-1) obtained according to the preceding 2-(a) and the mixture was made to react at room temperature for 16 hours. The same buffer as the one used in the preceding 2-(a) was used in this case. The conjugate (2-3) thus obtained was concentrated by ultrafiltration and then dialyzed against 0.9 sodium chloride solution.

2-(c) Cytotoxicity of conjugate against L 1210 cells

The cytotoxicity of the conjugate (2-3) obtained according to the preceding 2-(b) against the target L 1210 cells was examined.

0.9 ml of RPMI 1640 culture medium (containing 10% fetus bovine serum, 20 mM 2-mercaptoethanol and 0.1 mg/ml of kanamycin) containing 5×$10^4$ of L 1210 cells was placed in the wells of a 24-hole culture plate, to which 0.1 ml of test samples diluted to varied concentrations were added. The culture was carried out at 37° C. in an atmosphere of 5% $CO_2$ for 48 hours and then

EXAMPLE 3

3-(a) Preparation of F(ab')$_2$ having introduced maleimide groups 0.05 ml of N,N-dimethylformamide containing 0.42 mg of N-hydroxysuccinimidyl-m-maleimidobenzoate was added to 1.14 ml of 10 mM sodium phosphate buffer (pH 6.5) containing 10 mg of F(ab')$_2$ obtained according to Referential Example (b), and the mixture was made to react at room temperature for 40 minutes. After the reaction was over, the solution was put to Sephadex G-25 column (1 cm×30 cm, the same buffer used above) to remove the excess reagent, thus resulting F(ab')$_2$ having m-maleimidobenzoyl groups introduced thereinto.

3-(b) Preparation of conjugate having cytotoxicity (3-3) by reaction of F(ab')$_2$ having introduced m-maleimidobenzoyl groups (3-1) with poly-L-glutamate-L-alanine copolymer having thiol group and linked melphalan (3-2)

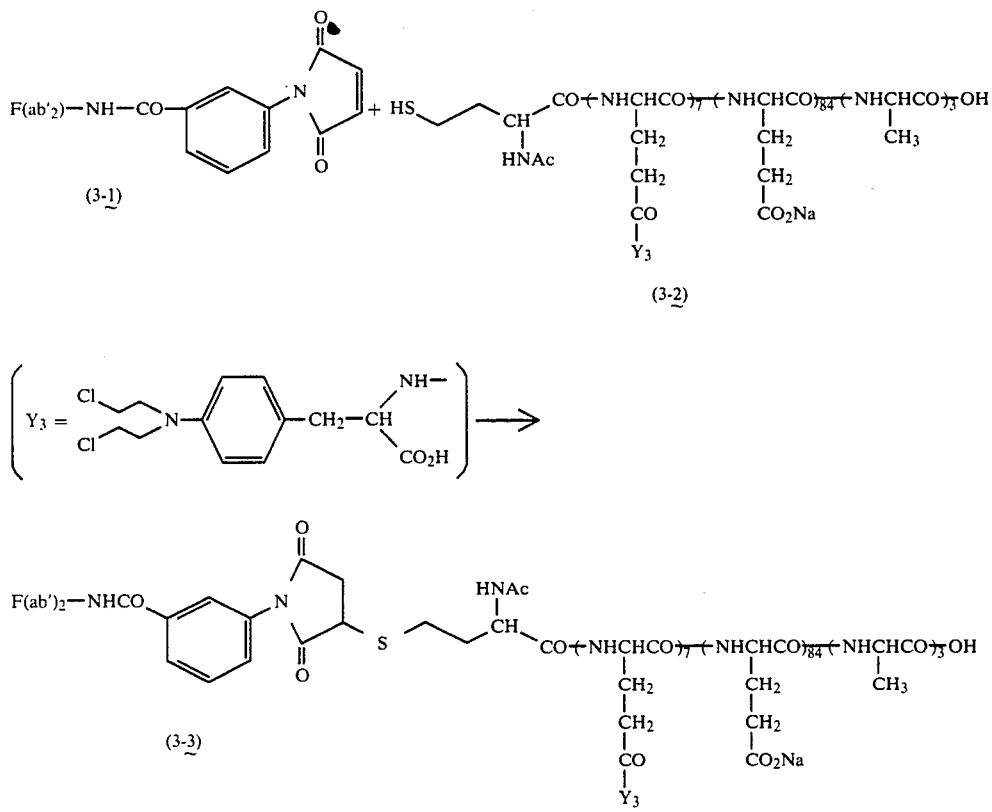

4.0 ml of a solution containing 4.7 mg of F(ab′)₂ having introduced m-maleimidobenzoyl groups (3-1) obtained according to the aforementioned 3-(a) was admixed with 0.40 ml of 10 mM sodium phosphate buffer containing poly-L-glutamate-L-alanine copolymer having a thiol group and linked to melphalan (3-2) (terminal SH equivalent to $1.6 \times 10^{-7}$ mole/ml) and the admixture was allowed to react at 4° C. for 16 hours. The hybrid thus obtained (3-3) was concentrated by ultrafiltration and dialyzed against 0.9% sodium chloride solution.

3-(c) Cytotoxicity of hybrid against L 1210 cells

The cytotoxicity of the hybrid (3-3) obtained according to the preceding 3-(b) against the target L 1210 cells was examined.

0.9 μl of RPMI 1640 culture medium (containing 10% fetus bovine serum, 20 μM 2-mercaptoethanol and 0.1 mg/ml of kanamycin) containing $5 \times 10^4$ L 1210 cells was placed in each centrifuge tube and 0.1 ml of test samples diluted to varied concentrations were added thereto. Preincubation was carried out at 37° C. for 20 minutes, followed by centrifugation and removal of the supernatant. After adding 1 ml of the abovementioned culture medium, the culture was further continued at 37° C. in an atmosphere of CO₂ for 48 hours. When the culture was over, the viable cells were counted by dye exclusion with Trypan Blue.

The result is shown in Table 3, from which it is confirmed that the preincubation conducted with the use of the conjugate corresponding to 100 μM melphalan showed an effect of prohibiting the proliferation against L 1210 cells. It may safely be assumed that the contact between the conjugate and the target cells was created to a considerably high degree in the initial 20-minute stage of the experiment from the fact that a marked effect was obtained in spite of the removal of the sample drug at the end of the 20-minute preincubation. The culture was carried out in two groups and the values show their averages.

TABLE 3

| Melphalan concentration in hybrid (3-3) (μM) | Number of viable cells, after 48-hour culture × $10^{-4}$/ml |
|---|---|
| 0 | 42.9 |
| 10 | 40.1 |
| 100 | 20.7 |

EXAMPLE 4

4-(a) Preparation of Fab′ having maleimide group introduced 5.7 ml of 5 mM acetic acid buffer (containing 0.14M sodium chloride and 1 mM EDTA, pH 5.5) containing 10 mg of Fab′ having 1 free thiol group obtained according to Referential Example (c), was mixed with 2 ml of the same buffer containing 1.2 mg Of o-phenylenedimaleimide and the mixture was made to react at 30° C. for 60 minutes. Then the reaction mixture was subjected to Sephadex G-25 gel filtration column chromatography (1 cm×30 cm, by use of the same buffer as mentioned above) to remove the excess reagent.

4-(b) Preparation of conjugate having cytotoxicity (4-3) by reaction of Fab′ having intorduced maleimide group (4-1) with poly-L-glutamate having thiol group and having linked are C (4-2)

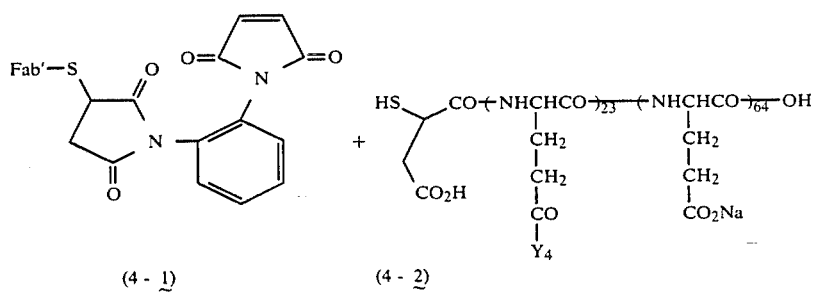

(4-1)  (4-2)

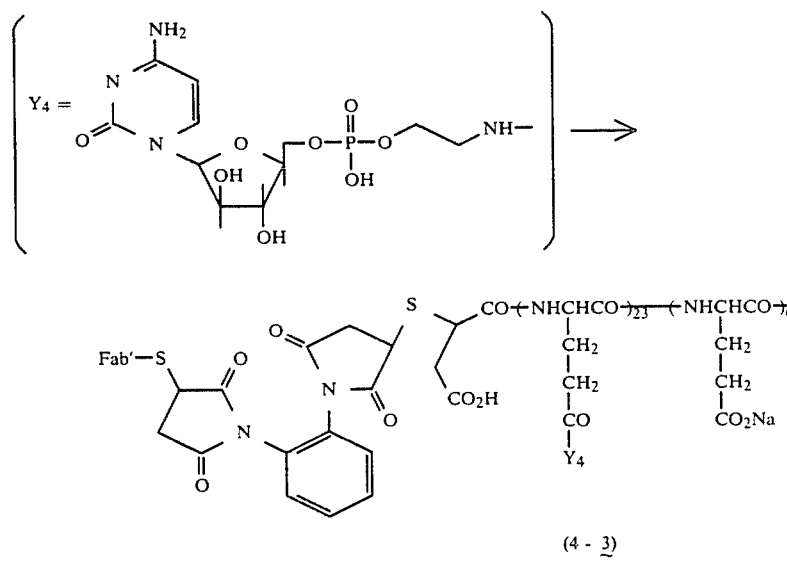

(4-3)

0.10 ml of the buffer described in 4-(a), containing poly-L-glutamate having a thiol group and linked Ara C (4-2) (terminal SH equivalent to $2.8 \times 10^{-7}$ mole/ml), and 1.0 ml of 0.4M sodium phosphate buffer (pH 6.5) were added to 5.1 ml of the solution containing 3.7 mg of Fab' modefind with o-phenylenedimaleimide (4-1) obtained in the above, and the mixture was allowed to react at 4° C. overnight. The conjugate thus obtained (4-3) was concentrated by ultra filtration and further dialyzed against 0.9% sodium chloride.

4-(c) Cytotoxicity of conjugate against L 1210 cells

The cytotoxicity of the conjugate (4-3) obtained in the preceding 4-(b) against the target L 1210 cells was examined according to the method described in Example 3-(c).

The result is shown in Table 4, which indicates that the conjugate of 10 µM Ara C eq. showed a reasonable cytotoxicity against L 1210 cells in preincubation tests.

TABLE 4

| Ara C concentration in conjugate (4-3) (µM) | Number of viable cells after 48-hour culture × $10^{-4}$/ml |
|---|---|
| 0 | 50.2 |
| 0.1 | 50.2 |

TABLE 4-continued

| Ara C concentration in conjugate (4-3) (µM) | Number of viable cells after 48-hour culture × $10^{-4}$/ml |
|---|---|
| 1 | 42.1 |
| 10 | 37.8 |

EXAMPLE 5

Preparation of conjugate having cytotoxicity (5-3) by reaction of IgMs fragment (5-1) with poly-L-glutamate having active disulfide group and linked daunomycin (5-2)

1 ml of a solution of IgMs fragment (5-1) obtained according to the method of Referential Example, (e), was admixed with 0.1 ml of a solution of sodium salt of poly-L-glutamate having an active disulfide group and linked daunomycin (5-2) (active disulfide equivalent weight $4.6 \times 10^{-7}$ mole/ml) and the admixture was allowed to react while being dialyzed against 50 mM glycine.sodium salt buffer (pH 9.2) containing 0.1M sodium chloride and 2 mM EDTA at 4° C. for 48 hours to obtain the desired hybrid (5-3). The reaction product was further dialyzed against 0.9% sodium chloride solution.

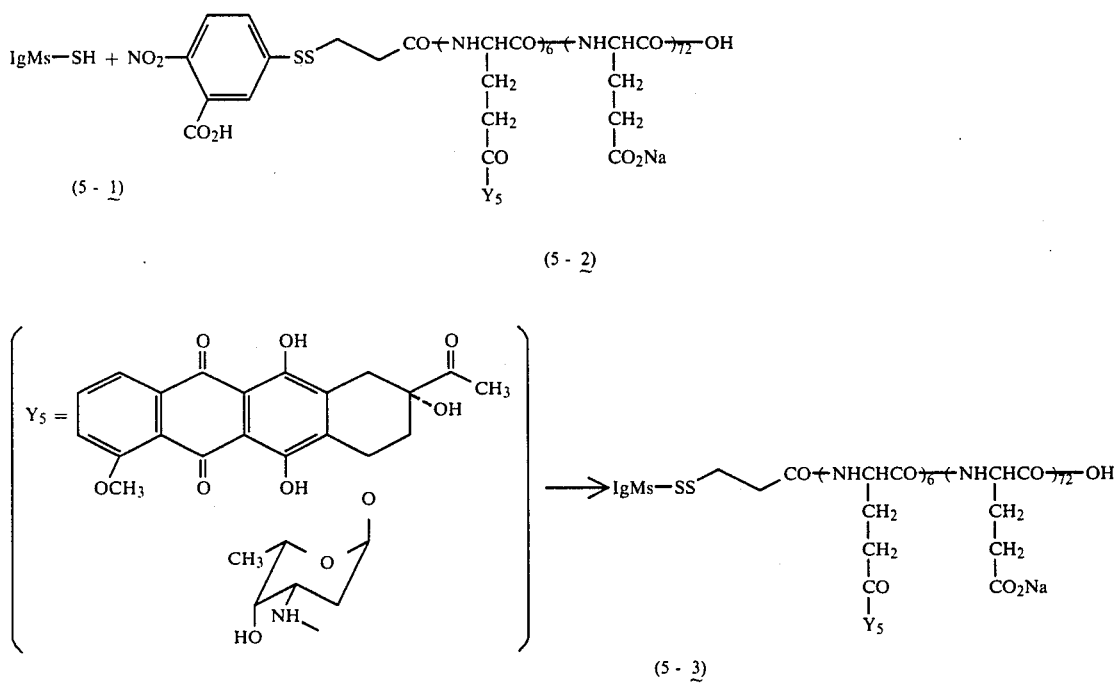

What is claimed is:

1. A conjugate having cytotoxicity comprising: (1) an immunoglobulin or a fragment, which is capable of selectively binding to a particular antigen possessed by a cell to be killed, and covalently bound thereto, via a carbonyl group at the amino terminal of a peptide polymer, by means of a bridge having at least one sulfur atom and a divalent linking group, (2) a peptide polymer having cytotoxic substances covalently bound to its side chain and having only one reactive group capable of covalently binding to said immunoglobulin, or its fragment, said reactive group being at one terminal of said polymer, and wherein said polymer is not an immunoglobulin.

2. The conjugate having cytotoxicity according to claim 1, wherein said conjugate is expressed by the following formula (I)

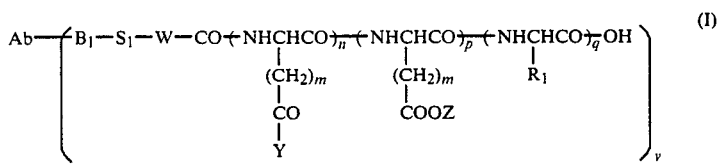

(wherein Ab indicates an immunoglobulin or its fragment capable of binding selectively to a particular antigen possessed by a cell to be killed; $B_1$ is a divalent organic group; $S_1$ is a sulfur atom; W is a divalent organic group; $R_1$ indicates a side chain at the α-position of α-amino acid or its derivative excluding a group which has a carboxyl group; Y represents a cytotoxic substance which contains a reacted amino group or imino group in the molecule; Z indicates a hydrogen atom or a monovalent cation; m is an integer 1 to 4; n, p, and q indicate the number of structural units, being $n=5$ to 1500, $p=0$ to 1500, and $q=0$ to 1500 respectively; and v indicates an integer 1 to 10).

3. The conjugate having cytotoxicity according to claim 1 or claim 2, wherein said conjugate is expressed by the following formula (II)

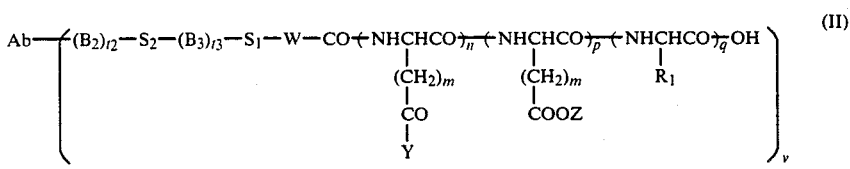

(wherein definitions of Ab, $S_1$, W, $R_1$, Y, Z, m, n, p, q, and v are the same as those given in case of formula (I) in claim 2; $S_2$ indicates a sulfur atom; $B_2$ and $B_3$ are divalent organic groups respectively; and $t_2$ and $t_3$ are identical with or different from each other, indicating 0 or 1).

4. The conjugate having cytotoxicity according to claim 1 or claim 2, wherein said conjugate is expressed by formula (III)

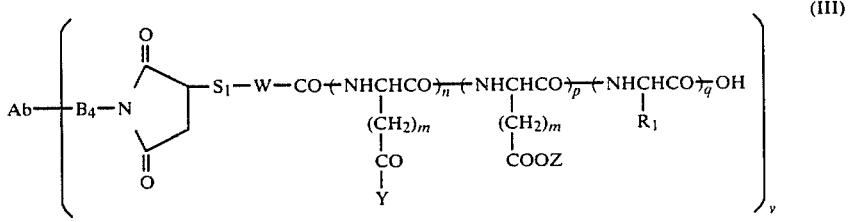

(wherein Ab, $S_1$, W, $R_1$, Y, Z, m, n, p, q, and v are as defined with regard to formula (I) of claim 2; and $B_4$ indicates a divalent organic group).

5. The conjugate having cytotoxicity according to claim 2, wherein w is an alkylene group having 1 to 4 carbon atoms in formula (I).

6. A process for the preparation of a conjugate having cytotoxicity expressed by the following formula (II-1)

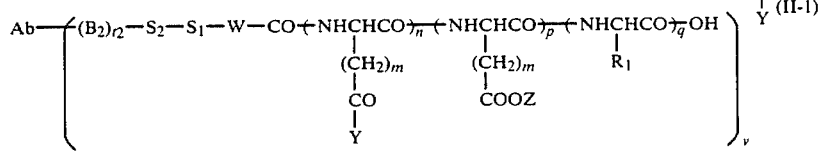

(wherein definitions of Ab, $S_1$, W, $R_1$, Y, Z, m, n, p, q, and v are the same as those given in case of formula (I) of claim 2; and $S_2$, $B_2$, and $t_2$ are as defined with regard to formula (II) of claim 3:) characterized by the reaction of a reactive polymer, which has cytotoxic substance linked thereto and also has an active disulfide group at the terminal of its molecule, expressed by the following formula (V)

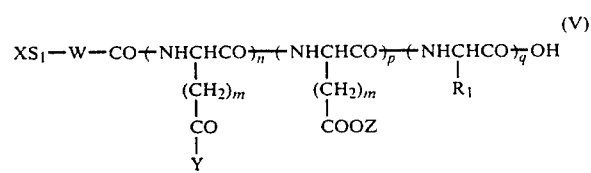

(wherein definitions of $S_1$, W, $R_1$, Y, Z, m, n, p, and q are the same as those given in case of formula (I) of claim 2; and X indicates a group which is capable of forming an active disulfide linkage) with an immunoglobulin or its fragment expressed by the following formula (IV) having a generated or introduced thiol group $$Ab-(B_2)_{t_2}-S_2H)_{v'} \quad (IV)$$

(wherein Ab is as defined with regard to formula (I) of claim 2; definitions of $S_2$, $B_2$, and $t_2$ are the same as those given with regard to formula (II) of claim 3; and v' is an integer 1 to 10).

7. A process for the preparation of a conjugate having cytotoxicity expressed by the aforementioned formula (II-1) of claim 6 characterized by the reaction of a reactive polymer expressed by the following formula (VII), which has a cytotoxic substance linked thereto and also has a thiol group at the terminal of its molecule,

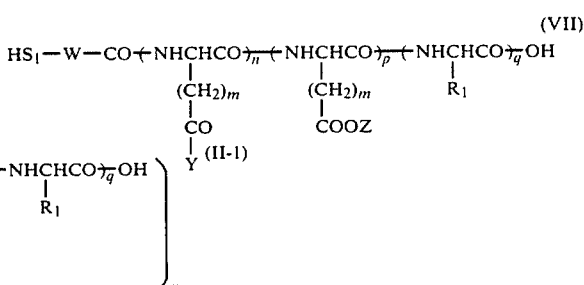

(wherein $S_1$, W, $R_1$, Y, Z, m, n, p, and q are as defined with regard to formula (I) of claim 2) with an immunoglobulin or its fragment expressed by the following formula (VI) having an induced or introduced active disulfide group $$Ab-(B_2)_{t_2}-S_2X)_{v'} \quad (VI)$$

(wherein Ab is as defined with regard to formula (I) of claim 2; $S_2$, $B_2$, and $t_2$ are as defined in case of formula (II) of claim 3; v' is as defined in case of formula (IV) of claim 6; and X is as defined with regard to formula (V) of claim 6).

8. A process for the preparation of a conjugate having cytotoxicity expressed by the following formula (II-2)

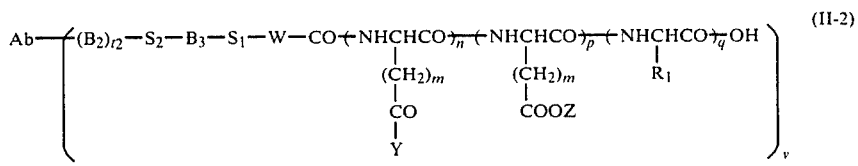

(wherein Ab, $S_1$, W, $R_1$, Y, Z, m, n, p, q, and v are as defined in case of formula (I) of claim 2 and $B_2$, $B_3$, and $t_2$ are as defined with regard to formula (II) of claim 3) characterized by covalently binding a reactive polymer, which has a cytotoxic substance linked thereto and also has a thiol group at the terminal of its molecule, expressed by the abovementioned formula (VII) of claim 7 to an immunoglobulin or its fragment, which has either a generated or introduced thiol group, expressed by the aforementioned formula (IV) of claim 6 by means of a cross linking agent which has 2 functional groups capable of reacting with a thiol group.

9. A process for the preparation of a conjugate having cytotoxicity expressed by the aforementioned formula (III) of claim 4 characterized by reacting a reactive polymer, which has a cytotoxic substance linked thereto and also has a thiol group at the terminal of its molecule, expressed by the aforementioned formula (VII) of claim 7 with an immunoglobulin or its fragment, which has a maleimide group introduced thereto, expressed by the following formula (VIII)

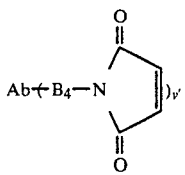

(wherein definition of Ab is the same as that given in case of formula (I) of claim 2; v' has the meaning given in case of formula (IV) of claim 6; and $B_4$ is as defined with regard to formula (III) of claim 4).

10. The conjugate having cytotoxicity according to claim 3, wherein w is an alkylene group having 1 to 4 carbon atoms in formula (II).

11. The conjugate having cytotoxicity according to claim 4, wherein w is an alkylene group having 1 to 4 carbon atoms in formula (III).

* * * * *